United States Patent [19]

Frank et al.

[11] Patent Number: 4,555,396

[45] Date of Patent: Nov. 26, 1985

[54] USE OF PYRYLIUM AND THIAPYRYLIUM COMPOUNDS AS BIOLOGICAL STAINS

[75] Inventors: David S. Frank, Rochester; Robert T. Belly, Webster, both of N.Y.

[73] Assignee: Eastman Kodak Company, Rochester, N.Y.

[21] Appl. No.: 452,260

[22] Filed: Dec. 22, 1982

[51] Int. Cl.[4] ............ G01N 1/30; C12Q 1/04; C09B 57/00

[52] U.S. Cl. ............ 424/3; 435/34; 549/13; 549/28; 549/356; 549/424

[58] Field of Search .............. 435/34, 29; 424/3, 7.1; 549/13, 28, 356, 424; 8/506, 516, 517

[56] References Cited

U.S. PATENT DOCUMENTS

| | | |
|---|---|---|
| 3,141,770 | 7/1964 | Davis et al. |
| 3,148,067 | 9/1964 | Reynolds |
| 3,250,615 | 5/1966 | Van Allan et al. |
| 3,271,257 | 9/1966 | Averette, Jr. |
| 3,497,690 | 2/1970 | Wheeless, Jr. et al. |
| 3,579,345 | 5/1971 | Jones |
| 3,684,377 | 8/1972 | Adams et al. |
| 3,822,270 | 7/1974 | Reynolds |
| 3,883,247 | 5/1975 | Adams |
| 3,938,994 | 2/1976 | Reynolds et al. |
| 4,025,349 | 5/1977 | Mee |
| 4,094,745 | 6/1978 | Scholefield |
| 4,173,473 | 11/1979 | Petropoulos et al. |
| 4,226,868 | 10/1980 | Zigman et al. |
| 4,232,121 | 11/1980 | Gilman, Jr. et al. |
| 4,256,458 | 3/1981 | Degen et al. ............ 8/506 |
| 4,353,824 | 10/1982 | Schindler et al. ............ 435/34 X |

FOREIGN PATENT DOCUMENTS

| | | |
|---|---|---|
| 4061 | 9/1979 | European Pat. Off. |
| 1560729 | 2/1980 | United Kingdom |
| 2074340 | 10/1981 | United Kingdom |

OTHER PUBLICATIONS

Habicht et al., "Carbocyanine Dyes Stain the Sarcoplasmic Reticulum of Beating Heart Cells", Exp. Cell. Res., 125:514–518 (1980).

Okimasu et al, Kanko Shikiso (Kyoto) 87: 33 (1979).

Todd-Sanford, "Clinical Diagnosis by Laboratory Methods," 15th Edition, edited by Davidsohn and Henry, (1974), pp. 177–178.

Blume, Glade, and Chessin, "Euchrysine, A Supravital Fluorescent Lysosomal Stain: Technic and Application for Hematologic Investigation," Blood, 33(1) pp. 87–99 (1969).

Bereiter-Hahn, "Dimethylaminostyrylmethylpyridiniumiodine (DASPMI) as a Fluorescent Probe for Mitochondria In Situ," Biochimica et Biophysica Acta, 423:1–14 (1976).

Green et al., "Simultaneous Differential Staining by a Cationic Carbocyanine Dye of Nucleic Acids, Proteins, and Conjugated Proteins," The Journal of Histochemistry and Cytochemistry, 22:767–781 (1974).

Primary Examiner—Robert J. Warden
Assistant Examiner—Randall E. Deck
Attorney, Agent, or Firm—J. Lanny Tucker

[57] ABSTRACT

Disclosed herein is an improvement in a method for distinguishing cells in a biological sample by staining with a dye, wherein the improvement comprises employing as the dye a compound of the formula

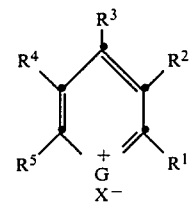

wherein
G is O or S;
$R^1$, $R^3$, and $R^5$ are independently selected from the group consisting of hydrogen, alkyl, aryl, aralkyl, amino, styryl, bis(diaryl)vinylene, and

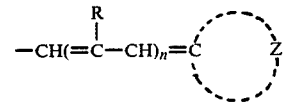

wherein
R is hydrogen or alkyl;
Z represents the elements necessary to complete a basic heterocyclic ring system of the type used in cyanine dyes;
n is 0 or 1;
$R^2$ is hydrogen or, taken together with either $R^1$ or $R^3$, represents the elements needed to complete an aromatic or a carbocyclic ring system;
$R^4$ is hydrogen or, taken together with either $R^3$ or $R^5$, represents the elements needed to complete an aromatic or a carbocyclic ring system; and
$X^-$ is an anion.

9 Claims, No Drawings

USE OF PYRYLIUM AND THIAPYRYLIUM COMPOUNDS AS BIOLOGICAL STAINS

BACKGROUND OF THE INVENTION

1. Field of the Invention

The present invention relates to biological strains. More particularly, the present invention relates to the use of pyrylium and thiapyrylium compounds as stains for biological cells and tissues.

2. Description of Related Art

The staining of biological cells and tissues with dyes, especially fluorochromic dyes, in order to differentiate one from another or simply to render them more easily observable under a microscope or other sensing means is well known in the art. Many of these dyes interact with the DNA or the RNA of the cell, or both, yielding products that fluoresce at different wavelengths, thereby being distinguishable. By such means it is possible to differentiate, for example, among the five types of peripheral blood leucocytes: neutrophils, eosinophils, basophils, lymphocytes, and monocytes; between cancerous and normal cells; and between mature and immature cells. Such differentiation enables the cytologist to diagnose certain disease states.

U.S. Pat. No. 3,684,377 describes a composition for the enumeration and differentiation of leucocytes. A suspension of fresh whole blood in a solution of Acridine Orange (Color Index 46005) having a pH factor and osmolality within normal physiological ranges for human blood is subjected to radiation from a blue laser. White cells are distinguished by detecting the resultant green fluorescence emitted by the stained nuclei of the leucocytes and differentiated by the amplitude of the red fluorescence emitted.

U.S. Pat. No. 3,883,247 describes a dye composition for the differential analysis of leucocytes comprising a hypotonic aqueous solution of a metachromatic fluorochrome, e.g., Acridine Orange (Color Index 46005). The hypotonic nature of the staining composition causes the rate of dye uptake by the leucocytes to differ among the various leucocyte types. Leucocytes are distinguished from other blood particles by the emission of green fluorescence, and the various types of leucocytes are differentially classified on the basis of different magnitudes of red and green fluorescences emitted.

Blum, R. S., Glade, P. R., and Chessin, L. N., "Euchrysine, A Supravital Fluorescent Lysosomal Stain: Technic and Application for Hematologic Investigation," Blood, 33(1):87-99, 1969 describes methods for the preparation of Euchrysine (Color Index 46040), an aminoacridine fluorescent supravital dye, into a form suitable for hematologic investigation and its use in the characterization of lysosomes in human peripheral blood, bone marrow, and established lymphoid cell lines (maintained in vitro).

U.S. Pat. No. 3,497,690 is directed to apparatus and a method for photoelectrically measuring size and fluorescent response of cells from biological material. The size of the cells, having been previously stained with a fluorochrome, such as Acridine Orange or Euchrysine, is determined by radiation scatter effect, and the fluorescent response of the cells, measured at a plurality of separate wavelengths, provides some indication of nucleic acid content of the cell.

The dyes employed in the above references, Acridine Orange or Euchrysine, have disadvantages in that they produce background fluorescence.

The use of certain styryl dyes as biological stains has been described in U.K. Published Application No. 2,074,340A and in Bereiter-Hahn, "Dimethylaminostyrylmethylpyridiniumiodine (DASPMI) as a Fluorescent Probe for Mitochondria In Situ", Biochimica et Biophysica Acta, 423:1-14, 1976.

Further, U.S. Pat. No. 4,232,121 describes a method for selecting machine dyes, especially cyanine dyes, that inhibit the growth of cells. Dyes containing a pyrylium nucleus are mentioned as being useful, among others. In the present work, it has also been noted that the compounds described herein are capable of inhibiting the growth of cells, especially somatic cells.

SUMMARY OF THE INVENTION

The present invention relates to the use of dyes, i.e. pyrylium and thiapyrylium compounds, that exhibit minimal background fluorescence and thus are advantageous for biological staining. These compounds are useful as both vital and fixed cell stains and they can be used without a wash step. They are especially useful for differentiation of biological cells and tissues. The compounds of the invention provide a wide range of absorption maxima in the visible range and many of them are fluorescent and exhibit a wide range of wavelengths that can be used for excitation and emission. Of these compounds, the preferred ones are metachromatic fluorochromes and produce unique staining of the cell nucleus and cytoplasm, which stain red and green, respectively.

More particularly, the present invention relates to an improvement in a method for distinguishing cells in a biological sample by staining with a dye, wherein the improvement comprises employing as the dye a compound of the formula

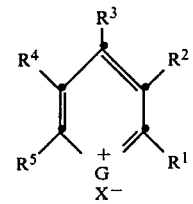

wherein

G is O or S;

$R^1$, $R^3$, and $R^5$ are independently selected from the group consisting of hydrogen, alkyl, aryl, aralkyl, amino, styryl, bis(diaryl)vinylene, and

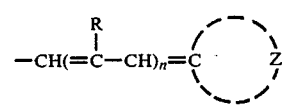

wherein

R is hydrogen or alkyl;

Z represents the elements necessary to complete a basic heterocyclic ring system of the type used in cyanine dyes;

n is 0 or 1;

$R^2$ is hydrogen or, taken together with either $R^1$ or $R^3$, represents the elements needed to complete an aromatic or a carbocyclic ring system;

$R^4$ is hydrogen or, taken together with either $R^3$ or $R^5$, represents the elements needed to complete an aromatic or a carbocyclic ring system; and $X^-$ is an anion.

DESCRIPTION OF THE PREFERRED EMBODIMENTS

The pyrylium and thiapyrylium dyes employed in the practice of this invention and methods for their preparation are known in the art, as described in, for example, U.S. Pat. No. 3,141,770; U.S. Pat. No. 3,148,067; U.S. Pat. No. 3,250,615; U.S. Pat. No. 3,579,345; U.S. Pat. No. 3,822,270; U.S. Pat. No. 3,938,994; and U.S. Pat. No. 4,173,473.

As stated above, $R^1$, $R^3$, and $R^5$ in the above formula can be the same or different and each can represent a hydrogen, an alkyl group, an aryl group, an aralkyl group, an amino group, a styryl group, a bis(diaryl)vinylene group, or a group of the formula:

wherein

R is hydrogen or alkyl;

Z represents the elements necessary to complete a basic heterocyclic ring system of the type used in cyanine dyes; and n is 0 or 1.

A person skilled in the art will understand that these groups can be substituted, if desired, with additional groups that will not interfere with the staining capacity of the compounds. For example, they may contain substituents such as alkyl, aryl, alkoxy, aryloxy, amino, substituted amino, and the like. Generally, it is preferable, where such substituents are used, to choose those that are not strongly electron withdrawing.

Where $R^1$, $R^3$, and/or $R^5$ are alkyl, it is preferred that they be alkyl of from 1 to 20 carbon atoms, i.e. methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, or an isomer of the foregoing. More preferably, where $R^1$, $R^3$, and/or $R^5$ are alkyl, they are chosen from among those groups having 1 to 4 carbon atoms. It is most preferred that such an alkyl substituent be methyl.

Where $R^1$, $R^3$, and/or $R^5$ are aryl, an aryl group of from 6 to 20 carbon atoms is preferred, for example, phenyl, 4-biphenyl, naphthyl, alkphenyl, such as 4-ethylphenyl, 4-propylphenyl, etc., alkoxyphenyl, e.g. 4-ethoxyphenyl, 4-methoxyphenyl, 4-amyloxyphenyl, 2-hexoxyphenyl, 2-methoxyphenyl, 2-amyloxyphenyl, 3,4-dimethoxyphenyl, etc., ω-hydroxyalkoxyphenyl, e.g., 2-hydroxyethoxyphenyl, 3-hydroxyethoxyphenyl, etc., 4-hydroxyphenyl, halophenyl, e.g., 3,4-dichlorophenyl, 3,4-dibromophenyl, 4-chlorophenyl, 2,4-dichlorophenyl, etc., aminophenyl, e.g., 4-diethylaminophenyl, 4-dimethylaminophenyl, 4-dibutylaminophenyl, 4-dioctylaminophenyl, etc.

Where $R^1$, $R^3$, and/or $R^5$ are aralkyl, it is preferred that the aryl group be phenyl or substituted phenyl and the alkylene group through which it is attached to the pyrylium or thiapyrylium ring have from 1 to 4 carbon atoms, e.g. methylene, ethylene, propylene, or butylene. It is most preferred that such an aralkyl group be benzyl.

When $R^1$, $R^3$, and/or $R^5$ are amine groups, they can be either primary, secondary, or tertiary amine groups.

Where $R^1$, $R^3$, and/or $R^5$ are

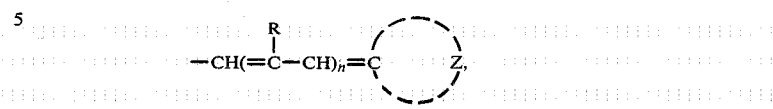

R can be either hydrogen or alkyl. Where it is alkyl, it is preferably an alkyl of from 1 to 4 carbon atoms, i.e. methyl, ethyl, propyl, butyl, or an isomer of the foregoing. Z represents the elements needed to complete a basic heterocyclic ring system of the type used in cyanine dyes. The heteroatom of the heterocyclic ring system is nitrogen, oxygen, sulfur, or selenium forming a nucleus such as: a thiazole nucleus, e.g., thiazole, 4-methylthiazole, 4-phenylthiazole, 5-methylthiazole, 5-phenylthiazole, 4,5-dimethylthiazole, 4,5-diphenylthiazole, 4-(2-thienyl)thiazole, benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 5-phenylbenzothiazole, 6-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-dioxymethylenebenzothiazole, 5-hydroxybenzothiazole, 6-hydroxybenzothiazole, naphthol[2,1-d]thiazole, naphthol[1,2-d]thiazole, 5-methoxynaphtho[2,3-d]thiazole, 5-ethoxynaphtho[2,3-d]thiazole, 8-methoxynaphtho[2,3-d]thiazole, 7-methoxynaphtho[2,3-d]thiazole, 4'-methoxythianaphtheno-7',6',4,5-thiazole, etc.; an oxazole nucleus, e.g., 4-methyloxazole, 4-phenyloxazole, 4,5-diphenyloxazole, 4-ethyloxazole, 4,5-dimethyloxazole, 5-phenyloxazole, benzoxazole, 5-chlorobenzoxazole, 5-methylbenzoxazole, 5-phenylbenzoxazole, 6-methylbenzoxazole, 5,6-dimethylbenzoxazole, 4,6-dimethylbenzoxazole, 5-methoxybenzoxazole, 5-ethoxybenzoxazole, 5chlorobenzoxazole, 6-methoxybenzoxazole, 5-hydroxybenzoxazole, 6-hydroxybenzoxazole, naphtho[2,1-d]oxazole, naphtho[1,2-d]oxazole, etc.; a selenazole nucleus, e.g., 4-methylselenazole, 4-phenylselenazole, benzoselenazole, 5-chlorobenzoselenazole, 5-methoxybenzoselenazole, 5-hydroxybenzoselenazole, tetrahydrobenzoselenazole, naphtho[2,1-d]selenazole, naphtho[1,2-d]selenazole; etc.; a thiazoline nucleus, e.g., thiazoline, 4-methylthiazoline, etc.; a pyridine nucleus, e.g. 2-pyridine, 5-methyl-2-pyridine, 4-pyridine, 3-methyl-4-pyridine, etc.; a quinoline nucleus, e.g. 2-quinoline, 3-methyl-2-quinoline, 5-ethyl-2-quinoline, 6-chloro-2-quinoline, 8-chloro-2-quinoline, 6-methoxy-2-quinoline, 8-ethoxy-2-quinoline, 8-hydroxy-2-quinoline, 4-quinoline, 6-methoxy-4-quinoline, 7-methyl-4-quinoline, 8-chloro-4-quinoline, 1-isoquinoline, 3,4-dihydro-1-isoquinoline, 3-isoquinoline, etc.; a 3,3-dialkylindolenine nucleus or a 3,3,5-trialkylindolenine nucleus e.g., 3,3-dimethylindolenine, 3,3,5-trimethylindolenine, etc.; or an imidazole nucleus, e.g., imidazole, 1-alkylimidazole, 1-alkyl-4-phenylimidazole, 1-alkyl-4,5-dimethylimidazole, benzimidazole, 1-alkylbenzimidazole, 1-aryl-5,6-dichlorobenzimidazole, 1-alkyl-1H-naphth[1,2-d]imidazole, 1-aryl-3H-naphth[1,2-d]imidazole, and 1-alkyl-5-methoxy-1H-naphth[1,2- d]imidazole, wherein the alkyl group has 1 to 4 carbon atoms and the aryl group 6 to 20 carbon atoms, etc.

In the above structural formula for the pyrylium and thiapyrylium dyes employed in the practice of this invention, $R^2$ can be hydrogen or taken together with either $R^1$ or $R^3$ can represent the elements needed to complete an unsubstituted or substituted aromatic or carbocyclic ring system. $R^4$ can be hydrogen or can be taken together with either $R^3$ or $R^5$ to represent the elements needed to complete an unsubstituted or substituted aromatic or carbocyclic ring system, such as benzene, naphthalene, dihydronaphthalene, tetralin, indene, benzocycloheptadiene, cyclohexane, and cyclopentane.

$X^-$ in the above structural formula is an anionic function including such anions such as perchlorate, tetrafluoroborate, paratoluenesulfonate, sulfonate, periodate, chloride, bromide, fluoride, iodide, sulfate, bisulfate, bisulfite, chloroaluminate, and chloroferrate.

Among the pyrylium and thiapyrylium salts that can be used in the practice of this invention are the following representative examples:

2,4,6-triphenylpyrylium perchlorate;
4-(4-methoxyphenyl)-2,6-diphenylpyrylium perchlorate;
4-(2,4-dichlorophenyl)-2,6-diphenylpyrylium perchlorate;
4-(3,4-dichlorophenyl)-2,6-diphenylpyrylium perchlorate;
2,6-bis(4-methoxyphenyl)-4-phenylpyrylium perchlorate;
6-(4-methoxyphenyl)-2,4-diphenylpyrylium perchlorate;
2-(3,4-dichlorophenyl)-4-(4-methoxyphenyl)-6-phenylpyrylium perchlorate;
4-(4-amyloxyphenyl)-2,6-bis(4-ethylphenyl)pyrylium perchlorate;
4-(4-amyloxyphenyl)-b 2,6-bis(4-methoxyphenyl)pyrylium perchlorate;
2,4,6-triphenylpyrylium fluoborate;
2,6-bis(4-ethylphenyl)-4-(4-methoxyphenyl)pyrylium perchlorate;
2,6-bis(4-ethylphenyl)-4-(4-methoxyphenyl)pyrylium fluoborate;
6-(3,4-diethoxystyryl)-2,4-diphenylpyrylium perchlorate;
6-(3,4-diethoxy-$\beta$-amylstyryl)-2,4-diphenylpyrylium tetrafluoborate;
6-(4-dimethylamino-$\beta$-ethylstyryl)-2,4-diphenylpyrylium fluoborate;
6-(1-n-amyl-4-p-dimethylaminophenyl-1,3-butadienyl)-2,4-diphenylpyrylium fluoborate;
6-(4-dimethylaminostyryl)-2,4-diphenylpyrylium fluoborate;
6-($\alpha$-ethyl-$\beta$,$\beta$-dimethylaminophenyl vinylene)-2,4-diphenylpyrylium fluoborate;
6-(1-butyl-4-p-dimethylaminophenyl-1,3-butadienyl)-2,4-diphenylpyrylium fluoborate;
6-(4-dimethylaminostyryl)-2,4-diphenylpyrylium perchlorate;
6-[$\beta$,$\beta$-bis(4-dimethylaminophenyl)vinylene]-2,4-diphenylpyrylium perchlorate;
2,6-bis(4-dimethylaminostyryl)-4-phenylpyrylium perchlorate;
6-($\beta$-methyl-4-dimethylaminostyryl)-2,4-diphenylpyrylium fluoborate;
6-(1-ethyl-4-p-dimethylaminophenyl-1,3-butadienyl)-2,4-diphenylpyrylium fluoborate;
6-[$\beta$,$\beta$-bis(4-dimethylaminophenyl)vinylene]-2,4-diphenylpyrylium fluoborate;
6-(1-methyl-4-p-dimethylaminophenyl-1,3-butadienyl)-2,4-diphenylpyrylium fluoborate;
4-(4-dimethylaminophenyl)-2,6-diphenylpyrylium perchlorate;
2,6-bis(4-ethylphenyl)-4-phenylpyrylium perchlorate;
2,6-bis(4-ethylphenyl)-4-methoxyphenylthiapyrylium fluoborate;
2,4,6-triphenylthiapyrylium perchlorate;
4-(4-methoxyphenyl)-2,6-diphenylthiapyrylium perchlorate;
6-(4-methoxyphenyl)-2,4-diphenylthiapyrylium perchlorate;
2,6-bis(4-methoxyphenyl)-4-phenylthiapyrylium perchlorate;
4-(2,4-dichlorophenyl)-2,6-diphenylthiapyrylium perchlorate;
2,4,6-tri(4-methoxyphenyl)thiapyrylium perchlorate;
2,6-bis(4-ethylphenyl)-4-phenylthiapyrylium perchlorate;
4-(4-amyloxyphenyl)-2,6-bis(4-ethylphenyl)thiapyrylium perchlorate;
6-(4-dimethylaminostyryl)-2,4-diphenylthiapyrylium perchlorate;
2,4,6-triphenylthiapyrylium fluoborate;
2,4,6-triphenylthiapyrylium bisulfate;
4-(4-methoxyphenyl)-2,6-diphenylthiapyrylium fluoborate;
2,4,6-triphenylthiapyrylium chloride;
2-(4-amyloxyphenyl)-4,6-diphenylthiapyrylium fluoborate;
4-(4-amyloxyphenyl)-2,6-bis(4-methoxyphenyl)thiapyrylium perchlorate;
2,6-bis(4-ethylphenyl)-4-(4-methoxyphenyl)thiapyrylium perchlorate;
4-anisyl-2,6-bis(4-n-amyloxyphenyl)thiapyrylium chloride;
2-[$\beta$,$\beta$-bis(4-dimethylaminophenyl)vinylene]-4,6-diphenylthiapyrylium perchlorate;
6-($\beta$-ethyl-4-dimethylaminostyryl)-2,4-diphenylthiapyrylium perchlorate;
2-(3,4-diethoxystyryl)-4,6-diphenylthiapyrylium perchlorate;
2,4,6-trianisylthiapyrylium perchlorate;
6-ethyl-2,4-diphenylpyrylium fluoborate;
2,6-bis(4-ethylphenyl)-4-(4-methoxyphenyl)thiapyrylium chloride;
6-[$\beta$,$\beta$-bis(4-dimethylaminophenyl)vinylene]-2,4-di(4-ethylphenyl)pyrylium perchlorate;
2,6-bis(4-amyloxyphenyl)-4-(4-methoxyphenyl)thiapyrylium perchlorate;
6-(3,4-diethoxy-$\beta$-ethylstyryl)-2,4-diphenylpyrylium fluoborate; and
6-(4-methoxy-$\beta$-ethylstyryl)-2,4-diphenylpyrylium fluoborate.

The following structural formulae illustrate compounds that have been found to be especially useful in the practice of the present invention. These compounds and the results obtained with them are described further in the examples below.

| Pyrylium and Thiapyrylium Salts |
|---|
Compound No. 1:
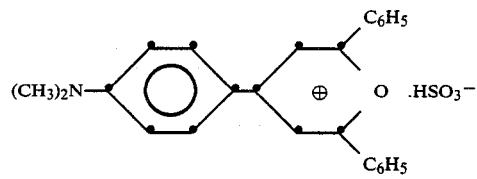
Compound No. 2:
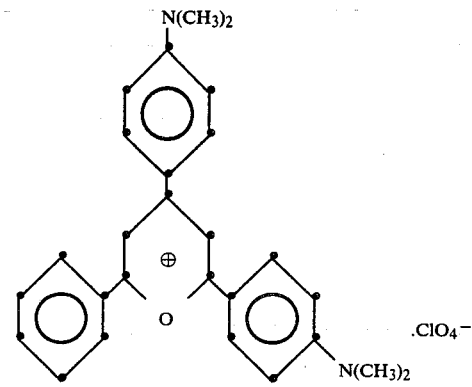
Compound No. 3:
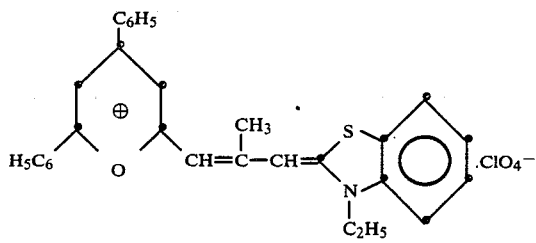
Compound No. 4:
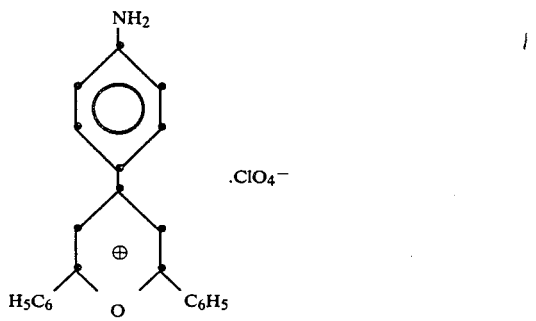
Compound No. 5:
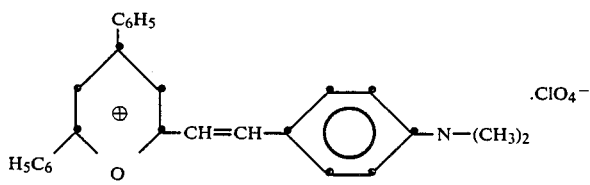

| Pyrylium and Thiapyrylium Salts |
|---|
Compound No. 6: 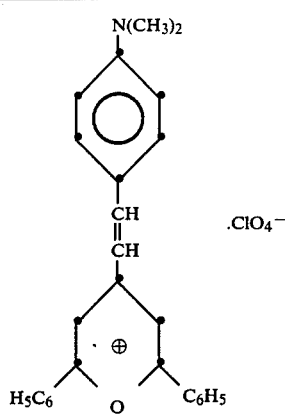
Compound No. 7: 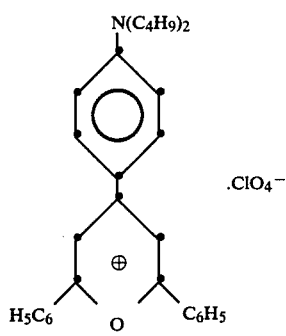
Compound No. 8: 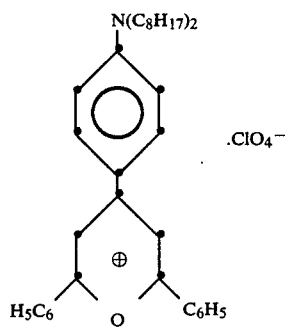
Compound No. 9: 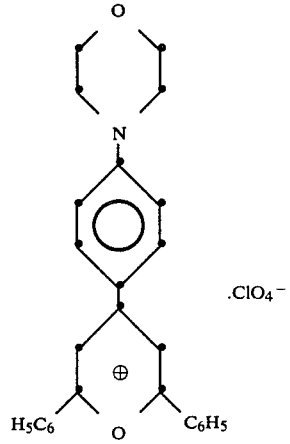

-continued
Pyrylium and Thiapyrylium Salts
Compound No. 10:
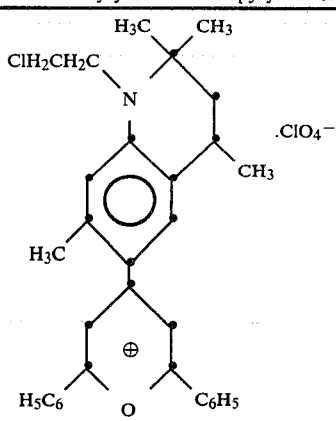
Compound No. 11:
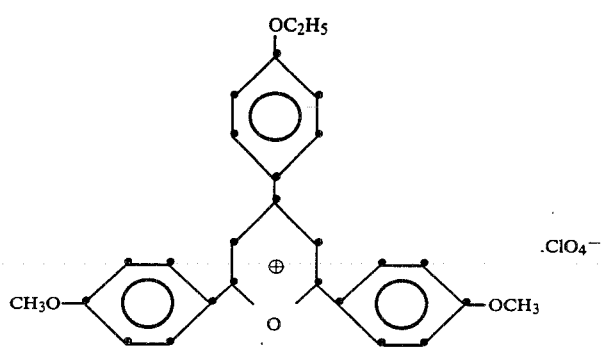
Compound No. 12:
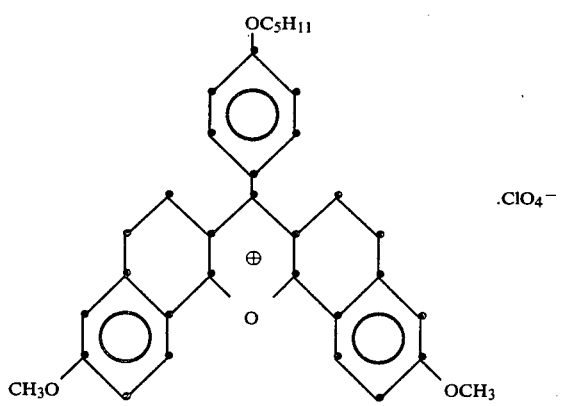
Compound No. 13:
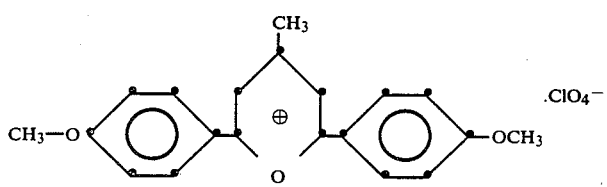
Compound No. 14:
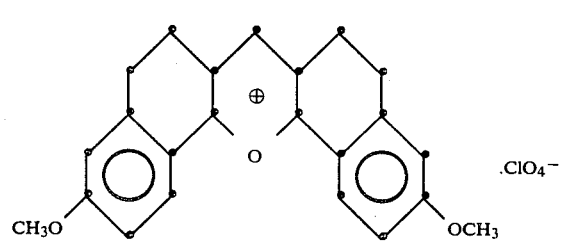

-continued
Pyrylium and Thiapyrylium Salts
Compound No. 15:
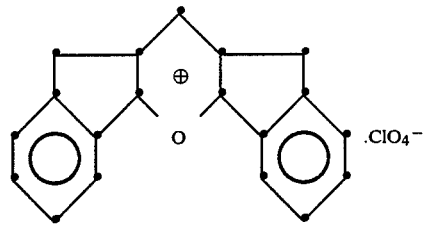
.ClO$_4^-$
Compound No. 16:
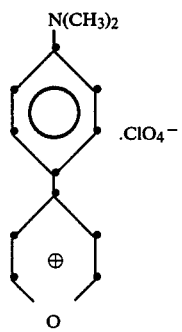
.ClO$_4^-$
Compound No. 17:
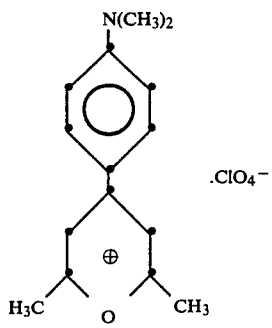
.ClO$_4^-$
Compound No. 18:
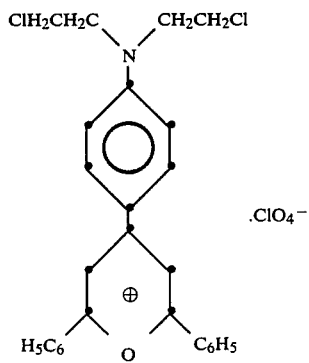
.ClO$_4^-$ -continued
Pyrylium and Thiapyrylium Salts
Compound No. 19:
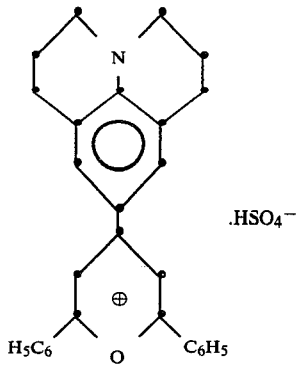
Compound No. 20:
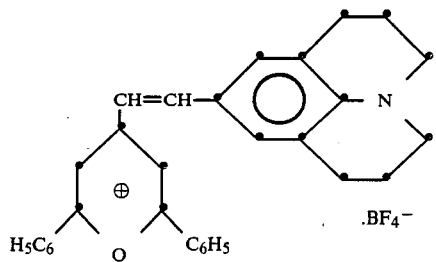
Compound No. 21:
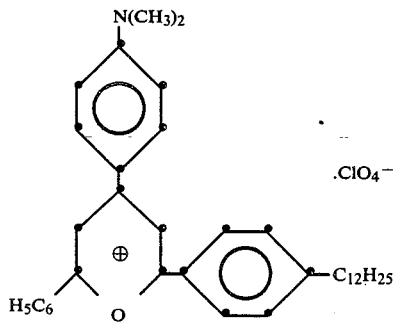
Compound No. 22:
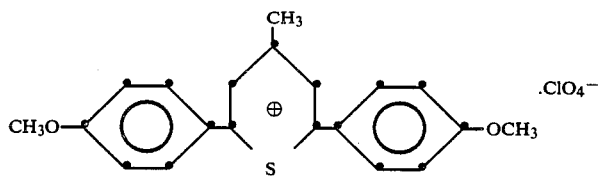
Compound No. 23:
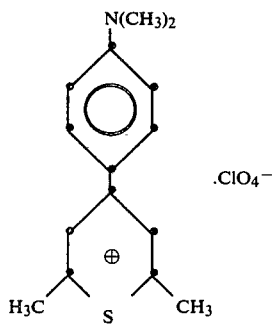

-continued
Pyrylium and Thiapyrylium Salts
Compound No. 24:
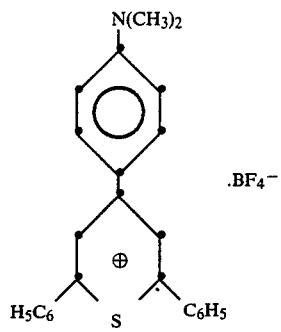
Compound No. 25:
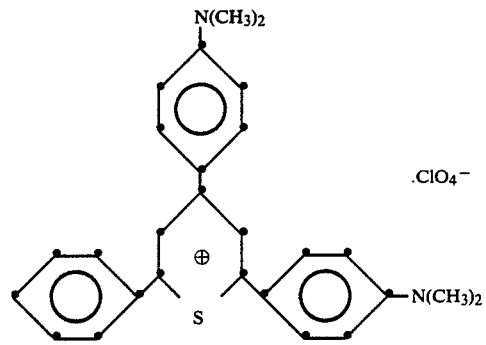
Compound No. 26:
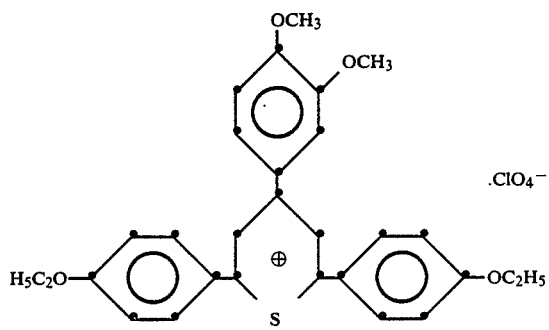
Compound No. 27:
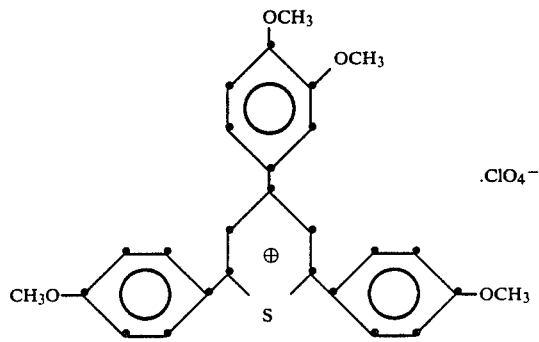

-continued
Pyrylium and Thiapyrylium Salts
Compound No. 28:
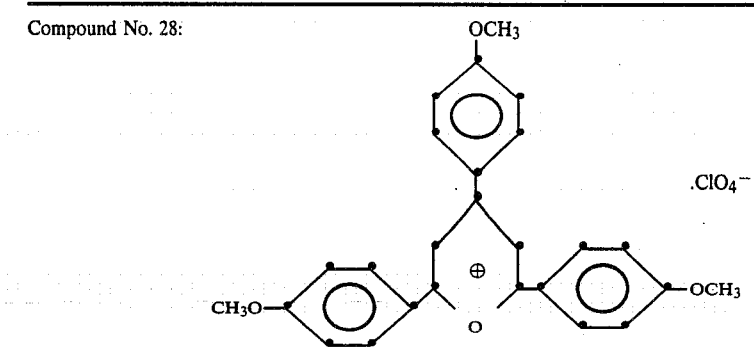
Compound No. 29:
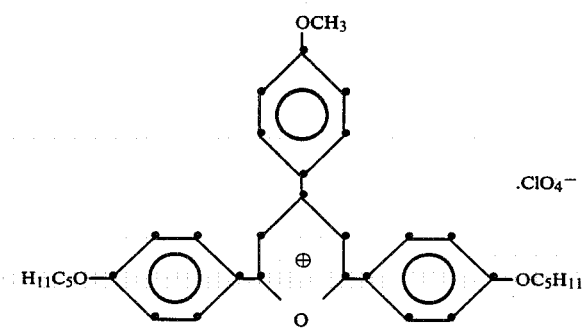
Compound No. 30:
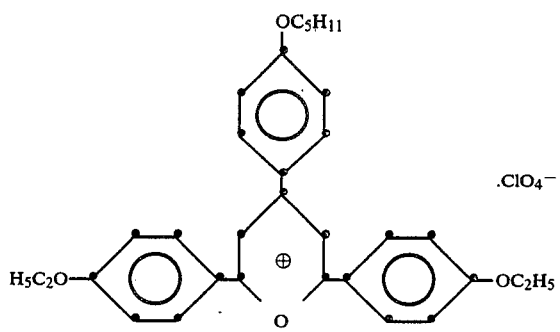
Compound No. 31:
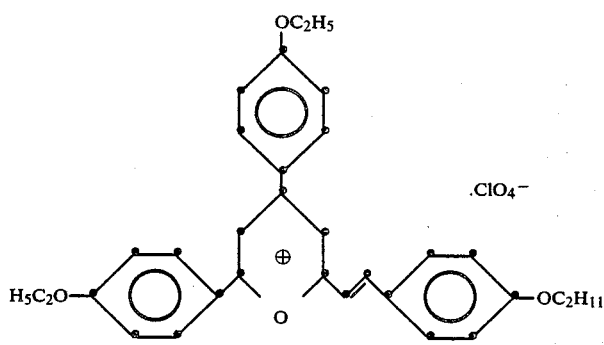
Compound No. 32:
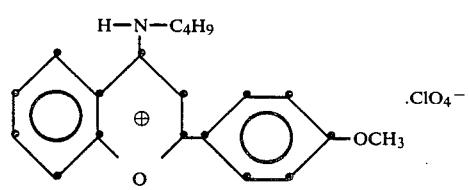

-continued
| Pyrylium and Thiapyrylium Salts |
|---|
Compound No. 33:
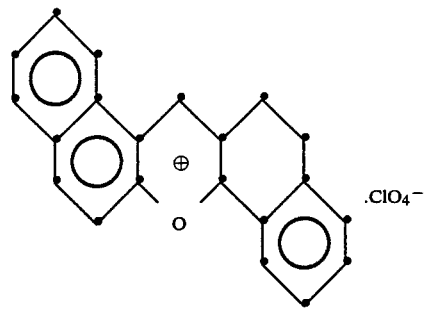
Compound No. 34:
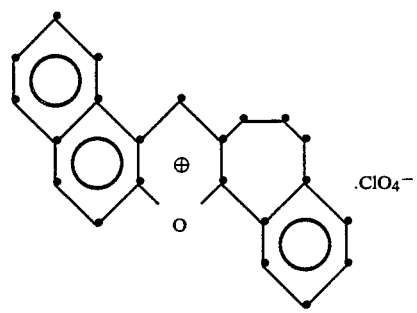
Compound No. 35:
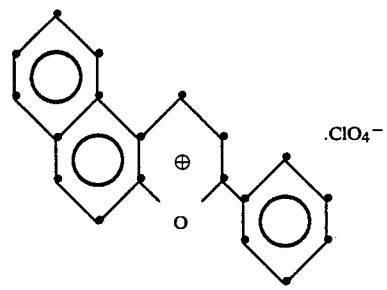
Compound No. 36:
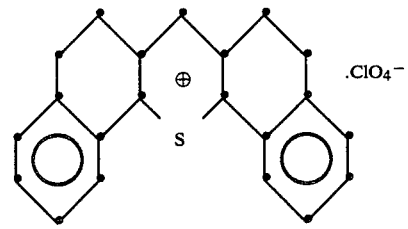
Compound No. 37:
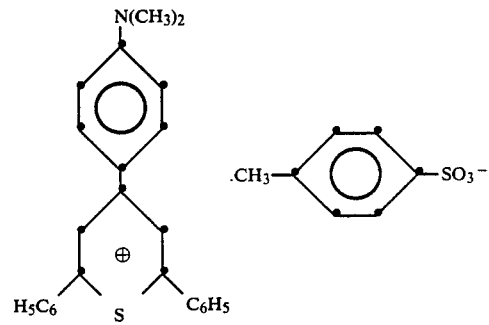

-continued
Pyrylium and Thiapyrylium Salts

Compound No. 38:

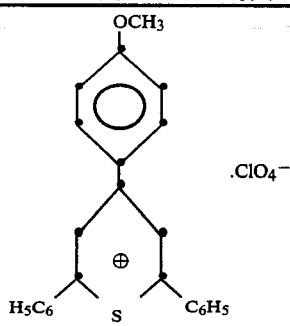

A. Materials

In the following examples, Dextran T70, Ficoll-Pacque, and Percoll were purchased from Pharmacia Fine Chemicals, Piscataway, NJ. ACD (acid, citrate, dextrose B-D 4606) prefilled blood collection tubes were purchased from VWR Scientific, Rochester, NY. Fetal calf serum, Raji cells (Burkitt's lymphoma), L-glutamine, and Roswell Park Memorial Institute 1640 medium [RPMI 1640 (Flow Laboratories, Inc., Product Catalog I, p. 126, 1977 description of composition medium)] were purchased from Flow Laboratories, McLean, VA. Permount TM mounting medium was purchased from Fisher Scientific, Rochester, NY. Gentamicin was purchased from Schering Corp., Union, NJ. Costar 96-well plates were purchased from Rochester Scientific, Rochester, NY. Fibroblasts (GM 1381) were purchased from Cell Repository, Camden, NJ, or American Type Culture Collection, Rockville, MD. Shandon Cytospin Cytocentrifuge was purchased from Shandon Southern Instruments, Inc., Sewickley, PA. All other chemicals were reagent grade, unless otherwise noted, and were obtained from Eastman Kodak Company, Rochester, NY.

B. Methods
Cell Purification and Vital Staining

Leukocyte-rich layers (buffy coats) were purified from blood of healthy adult donors (taken in ACD tubes) by adding 1.5 mL of Dextran T70 (6% in balanced salt solution, BSS) to a 10 mL tube of blood. This was allowed to sediment for approximately 1 hour after which the cells were washed 3 times in BSS. Cells were counted and adjusted to a final density of $10^6$ cells/mL.

Leukocytes were further fractionated following a procedure by Olofsson (Scandinavian Journal of Haemetology, 24:254, 1980), which resulted in a significant enrichment of the less abundant cell classes. The fractionation was carried out as follows: Percoll (colloidal silica, clad with biocompatible polyvinyl pyrrolidone) and a balanced salt solution (BSS) were mixed in varying proportions and layered in a tube to produce an 11-step density gradient (1.01–1.12 g/cc). A suspension of leukocytes (buffy coat) was applied to the top of the tube and sedimented at 1,600 xg for 20 minutes. Each cell class was detectable at its unique density step.

The table that follows compares the initial percentages of each cell class in the buffy coat layer with the percentage of each cell class within each fraction after fractionating the buffy coat layer. The fractionation especially improved the percentages of the low frequency cells, e.g., monocytes, eosinophils, and basophils. Enrichment factors for each class were obtained by dividing the percentage of enriched cells in each Percoll fraction by the percentage of corresponding cells in the initial buffy coat layer. Using this fractionation technique, the staining patterns of low frequency cells were better defined by microspectrofluorometry and flow cytometry.

| Cell Class | Buffy Coat Layer (No. of cells from each class per 100 cells in buffy coat sample) | Percoll Fractions (% cells from indicated class based on total no. of cells within each fraction | Enrichment Factors |
|---|---|---|---|
| Neutrophils | 58 | 88 | 1.5 |
| Lymphocytes | 32 | 95 | 3 |
| Monocytes | 6 | 50 | 8.3 |
| Eosinophils | 3 | 50 | 16.7 |
| Basophils | 1 | 15 | 15 |

Raji cells were also prepared for staining. An aliquot was removed from the continuous culture and centrifuged to remove old media. Fresh Roswell Park Memorial Institute Medium 1640 (RPMI 1640), supplemented with 10% fetal calf serum, L-glutamine, and gentamicin, was added. Cells were counted and adjusted to a density of $10^6$ viable cells/mL.

Two hundred microliters of buffy coat cells, fractionated leukocytes, or Raji cells at $10^6$ cells/mL was mixed with 200 µL of $10^{-5}$M dye. The cells were allowed to stand at room temperature for 15 minutes, and then slides were prepared by centrifugation in a Shandon Cytospin Cytocentrifuge for 5 minutes at 1500 RPM. After centrifugation, slides were removed and allowed to dry. Cover slips were placed over cells using Permount medium.

Fibroblasts were seeded on cover slips (22 mm²) in tissue culture plates (35 mm²) containing tissue culture medium. After 3–4 days of growth, when monolayers of fibroblasts were confluent, the medium was removed from the plates and replaced with 2 mL of $10^{-6}$M dye solution ($10^{-3}$M dye/methanol solution diluted with BSS). The plates were incubated at 37° C. for 10 minutes. The cover slips were removed, rinsed with BSS, and air dried. The cover slips were then mounted, cell side down, on glass slides with glycerol-BSS (9:1).

Cell Purification and Fixed Staining

Purified polymorphonuclear leukocyte preparations were obtained by layering the buffy coats described above on the Ficoll-Pacque, centrifuging for 30 minutes at 400 RCF (rotational centrifugal force) and washing three times with BSS. Cells were counted and adjusted to a density of $10^6$ cells mL.

Two hundred microliters of washed cell suspension from above was placed in the sample well of a Shandon Cytospin Cytocentrifuge and centrifuged at maximum speed for 10 minutes. The fixed cell preparations were air dried and stained for 1-2 minutes with $10^{-3}$M dye (in methanol) and washed with distilled water.

Microspectrofluorometry

Stained cell preparations were examined under a Zeiss Universal epifluorescence microscope. The filters used for evaluating the vitally stained cells are listed below and are indicated for each compound in Table I.

| Excitation | Dichroic Beam Splitter | Emission |
|---|---|---|
| 480 nm (Blue) | 510 nm | WR15* |
| 520 nm (Green) | 590 nm | 580 nm |

The method of the present invention for distinguishing cells can conveniently be carried out using conventional laboratory glassware, e.g., test tubes or glass slides. Alternatively, the dye can be incorporated into a matrix of absorbent material, such as a filter paper strip or a porous plastic lamina, by impregnation or otherwise, to yield a test element to which a cell sample can be applied. Such techniques are well-known to those skilled in the art.

EXAMPLE 1

Vital Staining Characteristics of Pyrylium and Thiapyrylium Compounds

Cells from buffy coat preparations and from tissue lines, e.g., lymphoma and fibroblast lines, were vitally stained, as described above, with pyrylium and thiapyrylium compounds, as listed in Tables I and II. The staining results are also listed in Tables I and II.

Pyrylium salt #1, a preferred compound exhibited marked metachromasia, i.e., leukocyte nuclear and cytoplasmic staining were observed at ~620 nm (red) and ~550 nm (green), respectively. Platelets and the filamentous cytoplasm of fibroblasts stained green.

TABLE I

Pyrylium Salts Vital Staining

| Compound No. | Filters | Cell Differentiation | | | Histologic Differentiation | |
|---|---|---|---|---|---|---|
| | | Buffy Coat | Lymphocytes | Polymorphs | Lymphoma | Fibroblasts |
| 1 | 480/510/WR15 | nucleus-red; cytoplasm-green at one pole of nucleus; platelets-green. | | | | cytoplasm-green; filamentous granules not stained. |
| 2 | 480/510/WR15 | | | nucleus-dark orange red; cytoplasm-light yellow. | | |
| 3 | 480/510/WR15 | | | | Raji cells-bright yellow green aggregates. | |
| 4 | 480/510/WR15 | nucleus-red cytoplasm-green to orange. Pronounced metachromasia (more than #1). | | | | |
| 5 | 520/590/580 | cytoplasm-bright orange flecks; some ruptured cells. | | | | |
| 6 | 520/590/580 | cytoplasm-medium bright orange flecks. | | | | |
| 7 | 480/510/WR15 | cytoplasm-bright green. | | | | |
| 8 | 480/510/WR15 | cytoplasm-dull green with some cells having bright green flecks. | | | | |
| 9 | 480/510/WR15 | | | | Raji cells-small cells: some have red nucleus; others stain completely bright orange; | nucleus-red, cytoplasm-bright green. |

TABLE I-continued

Pyrylium Salts
Vital Staining

| Compound No. | Filters | Cell Differentiation | | | Histologic Differentiation | |
|---|---|---|---|---|---|---|
| | | Buffy Coat | Lymphocytes | Polymorphs | Lymphoma | Fibroblasts |
| 10 | 480/510/WR15 | | | | large cells: nucleus-red; cytoplasm-medium green (grainy). Raji cells-small cells: yellow green, some very bright; large cells no staining. | |
| 11 | 480/510/WR15 | Dull orange (uniform). | | | | |
| 12 | 480/510/WR15 | cytoplasm-medium green; some ruptured cells. | | | | |
| 13 | 480/510/WR15 | | | granules-medium bright green. | | |
| 14 | 480/510/WR15 | | cytoplasm-medium green. | granules-medium green. | | |
| 15 | 480/510/WR15 | cytoplasm-dull green. | | | | |
| 16 | 480/510/WR15 | | platelets-apple green. | | Raji cells-small cells: apple green; large cells: no staining. | |
| 17 | 480/510/WR15 | | platelets-apple green. | | Raji cells-small cells: bright apple green; large cells: no staining. | |
| 18 | 480/510/WR15 | | | | small cells: bright yellow orange; large cells: cytoplasm-green. | |
| 19 | 480/510/WR15 | nucleus-dark red to black; cytoplasm-medium green. | | | | |
| 20 | 480/510/WR15 | nucleus-dark red to black; cytoplasm-medium green. | | | | |
| 21 | 480/510/WR15 | neutrophils-cytoplasm bright green. Some cells have red nucleus. Cells were destroyed. | | | | |

TABLE II

Pyrylium Salts
Vital Staining

| Compound No. | Filters | Cell Differentiation | | | Histologic Differentiation | |
|---|---|---|---|---|---|---|
| | | Buffy Coat | Lymphocytes | Polymorphs | Lymphoma | Fibroblasts |
| 22 | 480/510/WR15 | dull green. | | | | |
| 23 | 480/510/WR15 | | nucleus and cytoplasm-apple green. | | Raji cells-nucleus-apple green. | |
| 24 | 480/510/WR15 | | cytoplasm-some staining. | | Raji cells: nucleus-dark red. | |
| 25 | 480/510/WR15 | | | | Raji cells: nucleus-red; | |

TABLE II-continued

| | | Pyrylium Salts Vital Staining | | | Histologic Differentiation | |
|---|---|---|---|---|---|---|
| | | Cell Differentiation | | | | |
| Compound No. | Filters | Buffy Coat | Lymphocytes | Polymorphs | Lymphoma | Fibroblasts |
| | | | | | cytoplasm-green aggregates. | |
| 26 | 480/510/WR15 | | | nucleus-orange; other cells-dull green. | | |
| 27 | 480/510/WR15 | nucleus-green; | | nucleus-bright green. | | |

EXAMPLE 2

Cell Differentiation Using Pyrylium Salt #1 as the Stain

Pyrylium salt #1 was evaluated as a stain for differentiating human leukocytes. Fractions of these cells, separated on a Percoll density gradient, as described above, were stained with the abovementioned compound and evaluated by microspectrofluorometry and flow cytometry.

Fraction 2 contained two distinct cell populations, the eosinophils and the neutrophils. The eosinophils exhibited appreciably lower green fluorescence than the neutrophils. Fraction 3 contained only neutrophils.

Percoll cell fractions 7 and 8 were also evaluated by microspectrofluorometry. The distributions of fluorescent intensities showed that fraction 7 was pure lymphocytes, while fraction 8 included a lymphocyte population and an appreciable enrichment in monocytes.

Unfractionated human leukocytes were stained with pyrylium salt #1, resulting in three-peak distributions in each of the following when determined by flow cytometry: the green (~550 nm) vs the red (~620 nm), red vs light scatter and green vs light scatter domains.

EXAMPLE 3

Differentiation of Rabbit Reticulocytes Using Pyrylium Salt #1

Rabbit blood was fractionated on a Percoll density gradient described above. Fraction 2, obtained at 1.095 g/cc, was enriched in polychromatic cells (relative to normocytes) as shown by Wright's staining of a cytocentrifuge preparation of the cells. Cell density was adjusted to $10^6$ cells/mL as described above and the cells stained with $10^{-5}$M pyrylium salt #1 in Hanks' balanced Salt Solution (HBSS), without $Ca^{++}$ and $Mg^{++}$, for 15 minutes at room temperature. Microscopic examination of cytocentrifuge preparations of the stained cells showed a population of non-nucleated cells that exhibited filamentous projections that fluoresced green when excited with light at 480 nm. Counter-staining the same slide with Wright's Giemsa stain resulted in gray-violet-stained reticulocytes, which confirmed the above observations.

EXAMPLE 4

Fixed Cell Staining Characteristics of Pyrylium and Thiapyrylium Salts

Polymorphonuclear leukocytes were fractionated, fixed, and then stained, as described above, in "Methods", with pyrylium and thiapyrylium salts.

The staining properties of these compounds are summarized in Table III. At least three of the pyrylium salts (#13, 28, and 11) were extremely bright and showed specific nuclear fluorescent stains. Compounds #29 and #30 showed weaker nuclear fluorescence. In general, pyrylium salts, showing bright nuclear staining, contained methoxyphenyl groups. In addition to staining the nucleus, certain of the pyrylium salts stained either the entire cell (#31 and 14) or the cell cytoplasm (#32, 15, 12, 33, 34, and 35).

Certain of the thiapyrylium salts tested also showed bright and selective nuclear fluorescent staining (#26 and 27). Other thiapyrylium salts showed weaker, but also selective, nuclear staining (#22 and 36) as well as staining of the entire cell (#37 and 38).

TABLE III

| | Fixed Staining |
|---|---|
| Dye No. | Stained Polymorphonuclear Leucocytes (Fixed) |
| | Pyrylium Salt |
| 13 | Bright nuclear fluorescence |
| 28 | Bright nuclear fluorescence |
| 11 | Bright nuclear fluorescence |
| 29 | Nuclear fluorescence |
| 30 | Nuclear fluorescence |
| 31 | Bright fluorescence in entire cell |
| 14 | Bright nuclear fluorescence; cytoplasmic fluorescence (tends to fade) |
| 32 | Cytoplasmic fluorescence (fades rapidly) |
| 15 | Bright cytoplasmic fluorescence |
| 12 | Cytoplasmic fluorescence |
| 33 | Cytoplasmic fluorescence |
| 34 | Cytoplasmic fluorescence |
| 35 | Weak cytoplasmic fluorescence |
| | Thiapyrylium Salts |
| 26 | Bright nuclear fluorescence |
| 27 | Bright nuclear fluorescence |
| 22 | Nuclear fluorescence |
| 36 | Nuclear fluorescence; cytoplasmic fluorescence fades |
| 37 | Cytoplasmic, nuclear and granular fluorescence |
| 38 | Cytoplasmic and nuclear fluorescence |

The invention has been described in detail with particular reference to certain preferred embodiments thereof; it will be understood that variations and modifications can be effected within the spirit of the scope of the invention.

What is claimed is:

1. In a method for distinguishing cells in a biological sample by staining with a dye, wherein the improvement comprises employing as the dye a compound of the formula

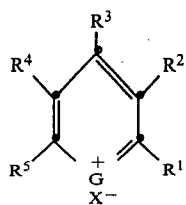

wherein

G is O or S;

$R^1$, $R^3$, and $R^5$ are independently selected from the group consisting of hydrogen, alkyl, aryl, aralkyl, amino, styryl and bis(diaryl)vinylene;

$R^2$ and $R^4$ are independently hydrogen; and $X^-$ is an anion.

2. The method of claim 1 wherein the cells are fixed prior to staining.

3. The method of claim 1 wherein the cells are vitally stained.

4. The method of claim 1 wherein the cells are leukocytes.

5. The method of claim 1 wherein the cells are reticulocytes.

6. The method of claims 1, 2, 3, 4, or 5 wherein the dye is a metachromatic fluorochrome.

7. The method of claim 1 wherein G is oxygen.

8. The method of claim 1 wherein G is sulfur.

9. The method of claim 1 wherein the dye is selected from the group consisting of:

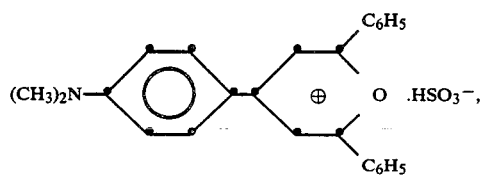

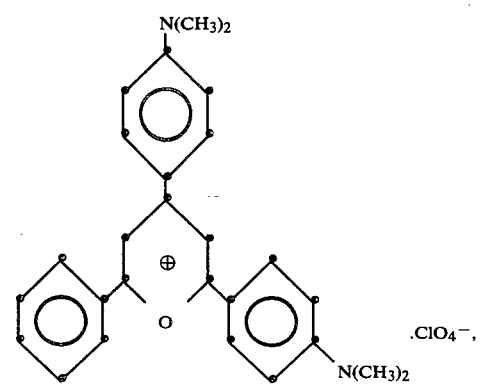

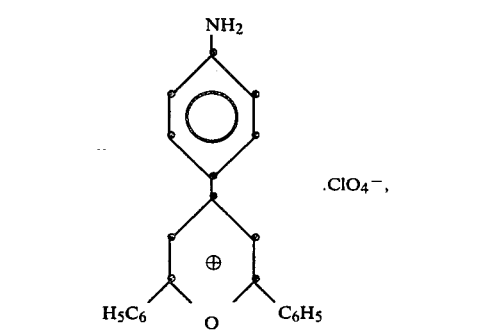

-continued

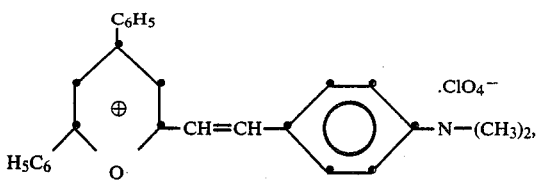

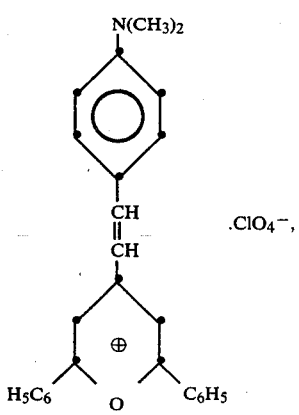

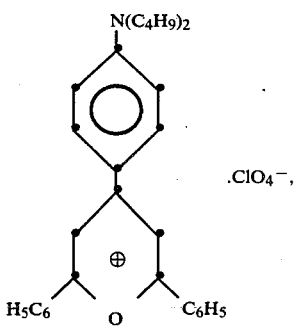

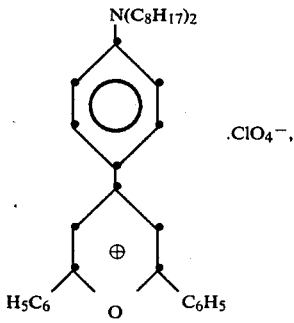

-continued
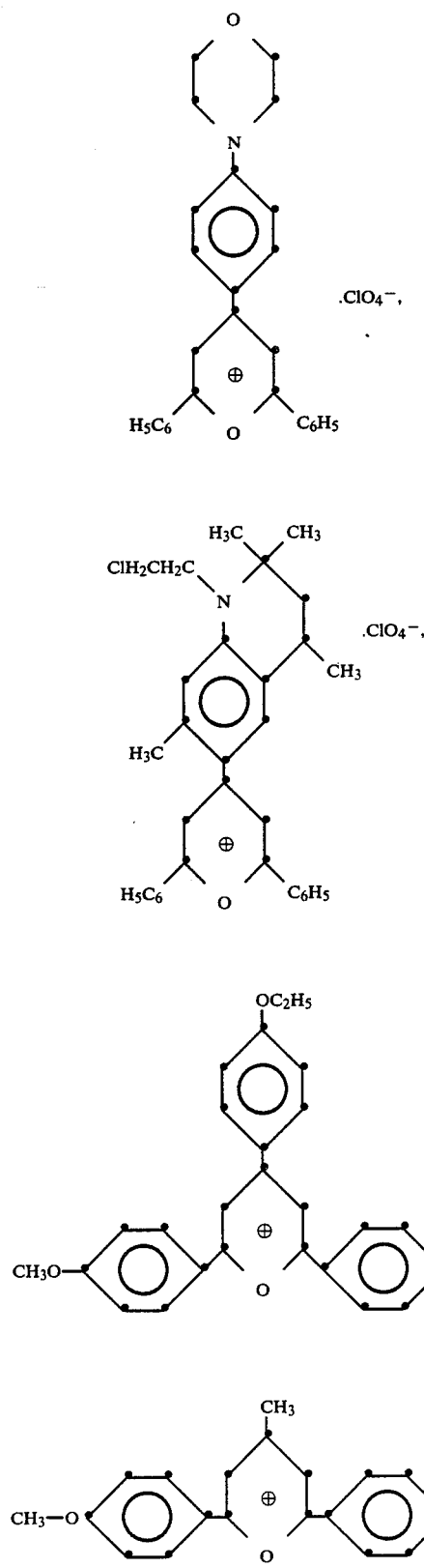
-continued
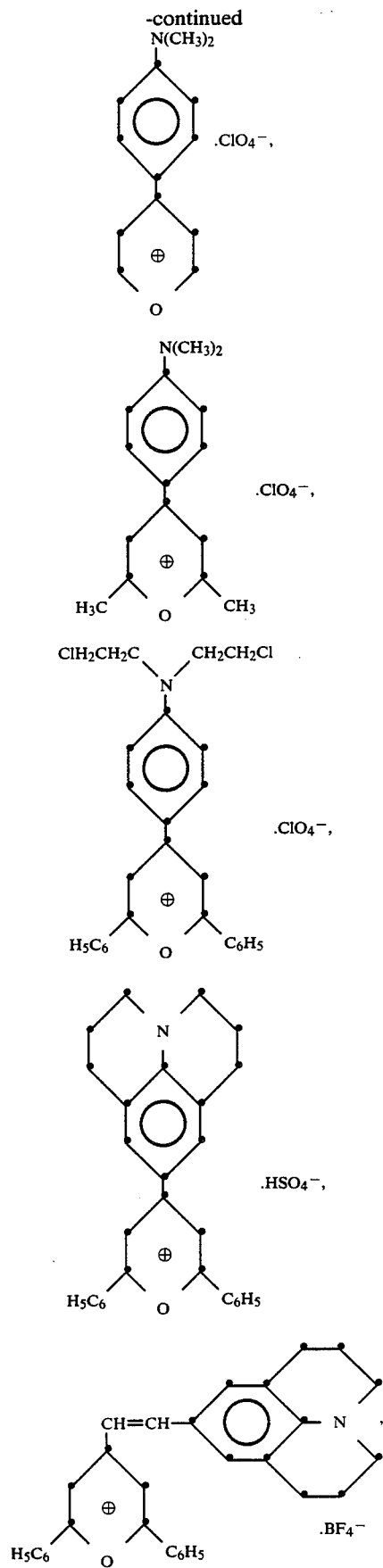

-continued
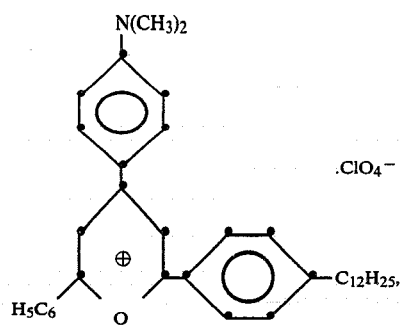
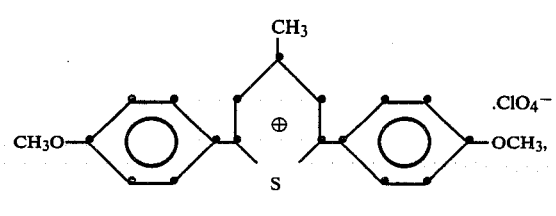
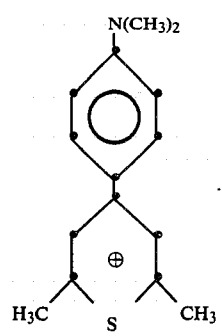
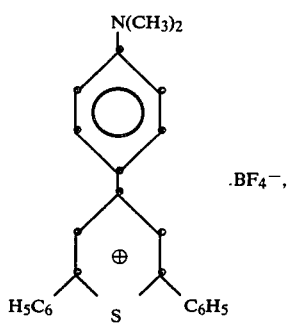
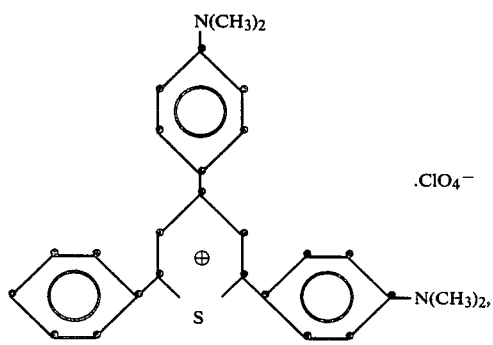
-continued
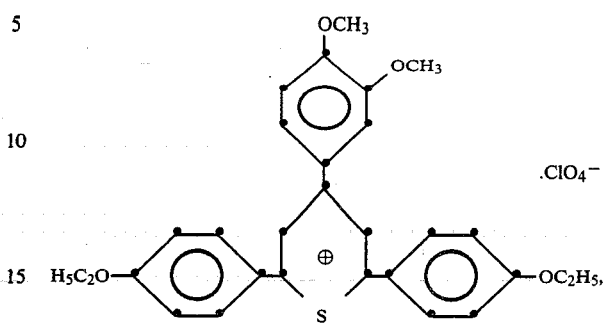
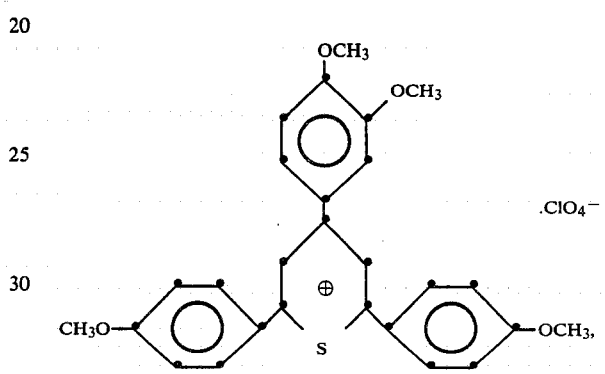
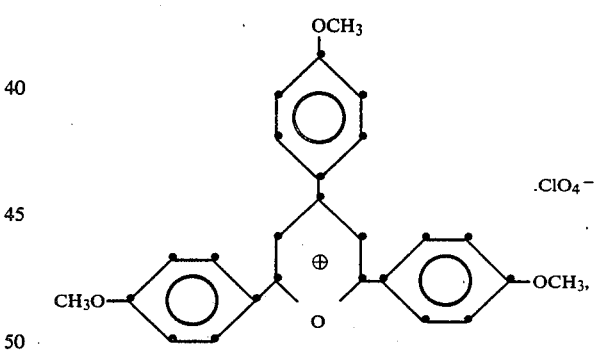
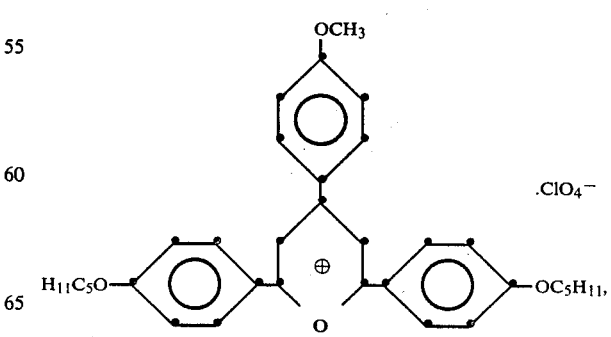

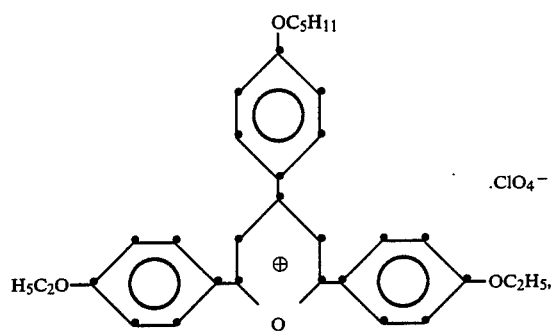
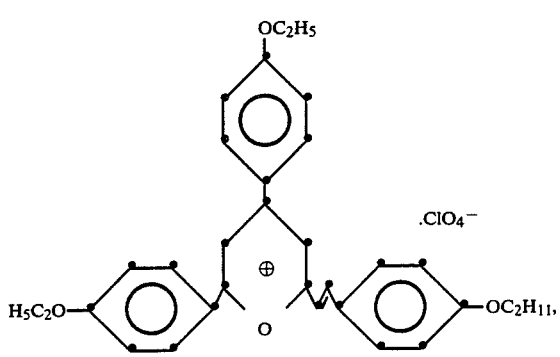
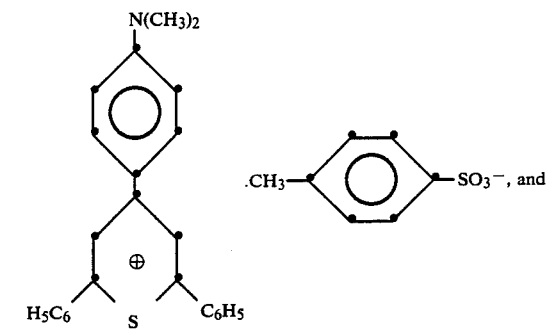
* * * * *